(12) United States Patent
Rogacs et al.

(10) Patent No.: US 9,057,673 B2
(45) Date of Patent: Jun. 16, 2015

(54) METHOD OF PREPARING RNA FROM RIBONUCLEASE-RICH SOURCES

(71) Applicant: The Board of Trustees of the Leland Stanford Junior University, Palo Alto, CA (US)

(72) Inventors: Anita Rogacs, Los Altos, CA (US); Juan G. Santiago, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/972,655

(22) Filed: Aug. 21, 2013

(65) Prior Publication Data

US 2014/0057247 A1    Feb. 27, 2014

Related U.S. Application Data

(60) Provisional application No. 61/693,235, filed on Aug. 24, 2012.

(51) Int. Cl.
| | |
|---|---|
| *C07H 21/00* | (2006.01) |
| *C12Q 1/68* | (2006.01) |
| *G01N 1/34* | (2006.01) |
| *C12N 15/10* | (2006.01) |
| *B01L 3/00* | (2006.01) |

(52) U.S. Cl.
CPC .............. *G01N 1/34* (2013.01); *C12N 15/1003* (2013.01)

(58) Field of Classification Search
CPC .................................................. C12N 15/1003
USPC ............ 435/6.1, 7.1, 7.2; 422/430; 536/25.41
See application file for complete search history.

(56) References Cited

U.S. PATENT DOCUMENTS

| | | |
|---|---|---|
| 5,981,235 A | 11/1999 | Shultz et al. |
| 2009/0269745 A1 | 10/2009 | Tonoike et al. |
| 2009/0317894 A1* | 12/2009 | Diges et al. ................... 435/270 |

OTHER PUBLICATIONS

Stratagene catalog, p. 39 1988.*
Birnboim et al. (1979) A rapid alkaline extraction procedure for screening recombinant plasmid DNA. Nucleic acids research 7 (6):1513-1523.
Liao et al. (2007) Development of an advanced electrochemical DNA biosensor for bacterial pathogen detection. J. Mol. Diagn. 9 (2):158-168.

(Continued)

*Primary Examiner* — Jezia Riley
(74) *Attorney, Agent, or Firm* — Jenny Buchbinder (57) ABSTRACT

Methods for preparing RNA from ribonuclease-rich sources while avoiding RNA degradation are described. The lysis protocol for ribonuclease-containing samples is performed at high pH to accelerate cell lysis and with a reducing agent that inactivates ribonucleases (RNases) by reducing disulfide bonds essential for RNase activity. Samples are briefly incubated for up to five minutes at high pH followed by addition of a reagent to lower the pH to a level at which the RNA is stable. This method of RNA extraction has many advantages over existing methods of RNA preparation, including that cell lysis is efficient, RNases are rapidly inactivated, and sample incubation times are short (less than 5 minutes), which protects RNA from degradation. The lysing procedure is performed entirely in aqueous solution with no heating, precipitations, or buffer exchanges required. Thus, a quick, simple procedure for extracting RNA is provided, which can easily be automated.

46 Claims, 3 Drawing Sheets

(56) References Cited

OTHER PUBLICATIONS

Bercavici et al. (2011) Rapid detection of urinary tract infections using isotachophoresis and molecular beacons. Analytical Chemistry 83 (11):4110-4117.

Singh et al. (2006) An alkaline solution simplifies nucleic acid preparation for RT-PCR and infectivity assays of viroids from crude sap and spotted membrane. J. Virol. Methods 132(1-2):204-211.

Desjardin et al. (1996) Alkaline decontamination of sputum specimens adversely affects stability of mycobacterial mRNA. J. Clin. Microbiol. 34(10):2435-2439.

* cited by examiner

METHOD OF PREPARING RNA FROM RIBONUCLEASE-RICH SOURCES

CROSS-REFERENCE TO RELATED APPLICATION

This application claims benefit under 35 U.S.C. §119(e) of provisional application 61/693,235, filed Aug. 24, 2012, which application is hereby incorporated by reference in its entirety.

STATEMENT REGARDING FEDERALLY SPONSORED RESEARCH OR DEVELOPMENT

This invention was made with Government support under contract N66001-09-C-2082 awarded by the Defense Advanced Research Projects Agency. The Government has certain rights in this invention.

TECHNICAL FIELD

The present invention pertains generally to methods of preparing RNA. In particular, the invention relates to an efficient method of extracting RNA from samples rich in ribonucleases that prevents degradation of RNA.

BACKGROUND

Currently, RNA is commonly prepared using guanidinium-based lysis followed by extraction with phenol-chloroform and precipitation with ethanol (Chomczynski et al. (1987) Analytical Biochemistry 162(1):156-159). For extraction of RNA from bacterial cells, enzymes (e.g., lysozyme), strong detergents (e.g., sodium dodecyl sulfate (SDS)), and chelating agents (e.g., ethylenediaminetetraacetic acid (EDTA) are also commonly used (Heptinstall *The Nucleic Acid Protocols Handbook*. R. Rapley, Ed. Humana Press: 2000; pp 47-52). Extraction mixtures typically have high ionic strengths (e.g., greater than 500 mM) and require careful purification or strong dilution, for example, by washing or buffer exchanges because the reagents used in RNA extraction, such as SDS, chaotropic agents, organic solvents, or alcohols are strong inhibitors of enzymes used in many standard experimental protocols in which RNA is used, such as PCR, restriction digestion, or ligation. In addition, current RNA extraction methods are notoriously time-consuming, tedious, and involve toxic reagents.

Although alkali lysis is widely used for isolation of plasmid DNA from bacterial cells (Birnboim et al. (1979) Nucleic acids research 7(6):1513-1523), it is not commonly used in isolating RNA because of the instability of RNA at high pH (Freitas et al. (2007) Molecular Biotechnology 36(2):151-158; Farrell (2005) RNA methodologies. Academic Press, Inc., San Diego, Calif.). Some groups have explored alkali-based RNA extraction from pelleted bacterial cells, though without providing adequate RNase control (Liao et al. (2007) J. Mol. Diagn. 9(2):158-168; Bercovici et al. (2011) Analytical Chemistry 83(11):4110-4117). If residual RNase activity is not eliminated, degradation of RNA will continue after lysis. Others have observed the lability of RNA in RNase-rich matrices, such as whole blood, where insufficient RNase inactivation results in severe degradation of RNA. For example, isolated RNA could no longer be amplified after incubation in blood plasma for as little as 15 seconds (Tsui, et al. (2002) Clinical Chemistry 48(10):1647-1653). Thus, adequate inactivation of RNases during cell lysis is clearly needed when preparing RNA from RNase-rich sources.

Schultz et al. (U.S. Pat. No. 5,981,235) proposed deactivating residual RNases using alkaline protease. In the method of Schultz et al., the RNA sample is suspended in a solution containing water, buffer and a chelating agent. The pH is adjusted to a value above 10 by adding a solution of sodium hydroxide. An anionic detergent and alkaline protease are added, and the solution is incubated for 5-30 minutes until nucleases are degraded. The pH of the solution is then lowered, and the RNA is isolated from the solution by precipitation with alcohol or using paramagnetic particles or a resin matrix containing silica particles in the presence of a chaotropic salt. The main disadvantages of this method is that the long incubation times required for preparing RNA from RNase-rich sources cause substantial degradation of the extracted RNA, and residual protease activity may interfere with further use of the extracted RNA.

Thus, there remains a need for a convenient, efficient method of preparing RNA that is free from degradation and contaminants.

SUMMARY

The present invention is based, in part, on the discovery of a new method for preparing RNA from ribonuclease-rich sources that minimizes RNA degradation. The lysis protocol for ribonuclease containing samples is performed at high pH to accelerate cell lysis and with a reducing agent that inactivates ribonucleases (RNases) by reducing disulfide bonds essential for RNase activity. RNases are rapidly inactivated by this method, allowing sample incubation times to be kept short (less than 5 minutes), which protects the RNA from degradation. This lysing procedure is performed entirely in aqueous solution with no heating, precipitations, or buffer exchanges required. Thus, a quick, simple procedure for extracting RNA is provided, which can easily be automated.

Thus, in one embodiment, the invention includes a method of preparing RNA from a biological sample, the method comprising: a) adding a reducing agent to the biological sample; b) adding a lysis solution to the biological sample to produce a mixture, wherein the lysis solution comprises a first reagent that causes the mixture to have a pH equal to or greater than 10; c) incubating the biological sample with the lysis solution for up to 5 minutes to produce a lysate; and d) adding a second reagent to the lysate to lower the pH of the lysate to a level at which the RNA is stable. The lysis solution may comprise the first reagent and the reducing agent, such that the first reagent and the reducing agent are added simultaneously to the biological sample. Alternatively, the reducing agent and the first reagent can be added separately to the biological sample. In certain embodiments, the first reagent and/or the second reagent are added to the biological sample by an electrochemical reaction at an electrode.

The first reagent used in the lysis solution may be a strong base, a weak base, or an amphoteric compound, such as an ampholyte. In one embodiment, the first reagent is a strong base such as, but not limited to, potassium hydroxide (KOH), sodium hydroxide (NaOH), barium hydroxide ($Ba(OH)_2$), cesium hydroxide (CsOH), strontium hydroxide ($Sr(OH)_2$), calcium hydroxide ($Ca(OH)_2$), lithium hydroxide (LiOH), and rubidium hydroxide (RbOH). In another embodiment, the first reagent is a weak base such as, but not limited to, Tris (tris(hydroxymethyl)aminomethane), N-ethylmorpholine, bis-tris-propane, creatine, imidazole, ammediol, arginine, lysine, ammonia, methylamine, dimethylamine, trimethylamine, diethylamine, diethylmethylamine, ethanolamine, and isoamylamine. In certain embodiments, the first reagent is an electrochemically generated base.

The reducing agent added to the biological sample may be a thiol such as, but not limited to, dithiothreitol (DTT), 2-mercaptoethanol (BME), and Tris(2-carboxyethyl)phosphine (TCEP).

The second reagent added to the biological sample may be a strong acid, a weak acid, or an amphoteric compound, such as an ampholyte. In one embodiment, the acid is a strong acid such as, but not limited to, hydrochloric acid, perchloric acid, sulfuric acid, nitric acid, and hydrobromic acid. In another embodiment, the acid is a weak acid such as, but not limited to, MOPS (3-(N-morpholino)propanesulfonic acid), MES (2-(N-morpholino)ethanesulfonic acid), PIPES (piperazine-N, N'-bis(2-ethanesulfonic acid)), HEPES ((4-(2-hydroxyethyl)-1-piperazineethanesulfonic acid)), TAPS (3-[[1,3-dihydroxy-2-(hydroxymethyl)propan-2-yl]amino]propane-1-sulfonic acid), tricine (N-(2-hydroxy-1,1-bis(hydroxymethyl)ethyl)glycine), cysteine, cacodylic acid, phosphoric acid, acetic acid, citric acid, formic acid, nitrous acid, carbonic acid, capric acid, caproic acid, and caprylic acid. In certain embodiments, the second reagent is an electrochemically generated acid.

In certain embodiments, the second reagent is added to the lysate after at least 5 seconds and up to 5 minutes after addition of the lysing solution, including any amount of time within this range, including at 1 minute, 2 minutes, 3 minutes, 4 minutes, or 5 minutes after addition of the lysing solution. The amount of the second reagent added to the lysate should be sufficient to lower the pH to a level at which the RNA is stable. The final pH of the lysate after adding the second reagent is preferably between pH 6 and pH 8.

Additional agents may be used to facilitate extraction and improve recovery of RNA from biological samples. For example, the lysis solution may further comprise one or more additional agents, such as detergents, chelating agents, denaturants, or carrier RNA, or any combination thereof. Alternatively, any of these agents can be added to the biological sample separately from the lysis solution.

In one embodiment, a detergent is added to the biological sample. Anionic, cationic, zwitterionic, or non-ionic detergents can be used such as, but not limited to, sodium dodecyl sulfate (SDS), N-laurylsarcosine, hexadecyltrimethylammonium bromide (CTAB), sodium tri-isopropylnaphthalene sulfonate, Tween 20, Tween 40, Tween 60, Triton X-100, sodium cholate, octylglucoside, sodium deoxycholate, dodecyldimethylamine oxide, CHAPS, CHAPSO, SB3-12, SB3-14, IGEPAL CA-630, Pluroinic F-68, Nonidet P40-substitute, Brij 35, n-dodecyl-β-D-maltoside, and octyl-β-D-glucopyranoside.

In another embodiment, carrier RNA is added to the biological sample. Carrier RNA may include polyinosinic acid, poly-A RNA, bacterial ribosomal RNA, bacterial or yeast transfer RNA, or other RNA that improves the recovery of the desired RNA.

In another embodiment, a chelating agent is added to the biological sample. Chelating agents that can be used include, but are not limited to, ethylene diamine tetraacetic acid (EDTA), ethylene bis(oxyethylenenitrilo)tetraacetic acid (EGTA), o-phenanthroline, and sodium 4-aminosalicylate.

In another embodiment, a denaturant is added to the biological sample. Denaturants that can be used include, but are not limited to, urea, guanidine thiocyanate (GndSCN), guanidine hydrochloride (GndHCL), and lithium perchlorate.

In one embodiment, the method further comprises adding lysozyme to the biological sample before adding the reducing agent.

In one embodiment, the method further comprises adding formamide.

The biological sample from which RNA is extracted can be a sample of cells, tissue, or fluid isolated from any prokaryotic or eukaryotic organism or virus. In certain embodiments, the RNA is prepared from bacteria, fungi, plants, protists, or animals. In certain embodiments, the RNA is prepared from a bodily fluid such as, but not limited to, blood, serum, plasma, urine, saliva, sputum, ascites, semen, bronchial lavage fluid, synovial fluid, and cerebrospinal fluid. In certain embodiments, the biological sample comprises viral RNA.

Any type of RNA can be prepared by the methods described herein, including but not limited to, messenger RNA, ribosomal RNA, transfer RNA, or regulatory RNA (e.g., small regulatory non-coding RNA, such as small interfering RNA (siRNA), microRNA (miRNA) and Piwi-associated RNAs (piRNA), and long non-coding RNA).

The lysis procedures described herein may be used alone or in combination with any other method for isolating or purifying RNA. For example, RNA may be further purified by immobilization on a solid support such as, but not limited to, RNA adsorbent beads, magnetic beads, or silica, or by gel filtration, reverse phase, ion exchange, or affinity chromatography. RNA can be isolated by phenol-chloroform extraction or precipitation with alcohol. Alternatively, an electric field-based method can be used to separate the desired RNA molecule from other molecules. Exemplary electric field-based methods include polyacrylamide gel electrophoresis, agarose gel electrophoresis, capillary electrophoresis, pulsed field electrophoresis, and isotachophoresis.

In another aspect, the invention includes a kit for isolating RNA comprising a lysis solution or reagents for preparing a lysis solution as described herein. The kit may further comprise a reducing agent, either separate or included in the lysis solution. The kit may also comprise one or more additional agents for further purification of RNA.

These and other embodiments of the subject invention will readily occur to those of skill in the art in view of the disclosure herein.

BRIEF DESCRIPTION OF THE FIGURES

FIG. 2 shows lysis efficiencies for incubation times of 5 minutes and 30 seconds. Formamide was used to aid protein solubilization. Detergents, such as Triton X-100 could also be used. The fraction of cells lysed (shown at left) was calculated from the number of initial cells (0 mM NaOH). The number of surviving cells (shown at right) was counted after incubation in solutions containing 40 mM, 120 mM and 250 mM NaOH.

FIG. 3 shows experimental demonstrations of the combined effect of reducing agent (DTT) and carrier RNA on ITP-based RNA purification from bacteria infected human blood. The bars show RT-qPCR, threshold cycles for 16S rRNA extracted from blood spiked with P. putida cells. All negative controls for RT-VCR (RNA extracted from uninfected blood) amplified above 30 cycles. We show results from four sets of experiments. Lysing in the presence of DTT and carrier RNA yielded consistent and low threshold amplification cycles for two different bacterial cell densities. In their absence, all bacterial RNA extractions failed, or were significantly compromised. We believe that the observed effect is primarily due to the presence of DTT. However, we hypothesize that carrier RNA would have a significant effect on extraction efficiency at very low RNA concentrations (which includes RNA from the background matrix). The latter hypothesis is supported by the typically higher variation in threshold target levels for the "no DTT, no carrier RNA" case at lower bacteria concentrations, such as the example data shown here. NA indicates no amplification within 40 cycles (Rogacs et al. (2012) Analytical Chemistry 84(14):5858-5863).

DETAILED DESCRIPTION

The practice of the present invention will employ, unless otherwise indicated, conventional methods of pharmacology, chemistry, biochemistry, recombinant DNA techniques and immunology, within the skill of the art. Such techniques are explained fully in the literature. See, e.g., A. L. Lehninger, *Biochemistry* (Worth Publishers, Inc., current addition); Sambrook, et al., *Molecular Cloning: A Laboratory Manual* ($3^{rd}$ Edition, 2001); *RNA: Methods and Protocols* (Methods in Molecular Biology, edited by H. Nielsen, Humana Press, 1st edition, 2010); Rio et al. *RNA: A Laboratory Manual* (Cold Spring Harbor Laboratory Press; 1st edition, 2010); Farrell *RNA Methodologies: Laboratory Guide for Isolation and Characterization* (Academic Press; $4^{th}$ edition, 2009); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "an RNA" includes a mixture of two or more RNA, and the like.

As used herein, a "biological sample" refers to a sample of cells, tissue, or fluid isolated from a prokaryotic or eukaryotic organism, including but not limited to, for example, blood, plasma, serum, fecal matter, urine, bone marrow, bile, spinal fluid, lymph fluid, sputum, ascites, bronchial lavage fluid, synovial fluid, samples of the skin, external secretions of the skin, respiratory, intestinal, and genitourinary tracts, tears, saliva, milk, organs, biopsies, and also samples of cells, including cells from bacteria, fungi, protists, plants, and animals as well as in vitro cell culture constituents, including but not limited to, conditioned media resulting from the growth of cells and tissues in culture medium, e.g., recombinant cells, and cell components, and also samples containing nucleic acids from viruses.

The term "about," particularly in reference to a given quantity, is meant to encompass deviations of plus or minus five percent.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of a new method for preparing RNA from ribonuclease-rich sources that avoids RNA degradation. RNA is extracted from ribonuclease-containing samples using a lysis protocol performed at high pH to accelerate cell lysis and with a reducing agent that inactivates ribonucleases by reducing disulfide bonds essential for activity (see Example 1). Samples are briefly incubated for up to five minutes at high pH followed by addition of a reagent, such as an acid or ampholyte, to lower the pH to a level at which the RNA is stable. This method of RNA extraction has many advantages over existing methods of RNA preparation, including that cell lysis is efficient, RNases are rapidly inactivated, and sample incubation times are short (less than 5 minutes), which protects RNA from degradation. The lysing procedure is performed entirely in aqueous solution with no heating, precipitations, or buffer exchanges required. Furthermore, this method avoids reagents commonly used for extraction of RNA, such as isopropanol, guanidinium hydrochloride, phenol, or $CsCl_2$, which inhibit enzymes (e.g., reverse transcriptases, polymerases, ligases, and endonucleases) used in downstream applications. Thus, a quick, simple procedure for extracting RNA is provided, which is compatible with most applications requiring the use of RNA, including PCR, ligation, transcriptome analysis, microarray analysis, northern analysis, and cDNA library construction.

In order to further an understanding of the invention, a more detailed discussion is provided below regarding this novel method of preparing RNA.

A. Method of RNA Preparation

In one aspect, the invention includes a method for preparing RNA from RNase-rich sources that minimizes degradation of RNA. In one embodiment, the method comprises: a) adding a reducing agent to the biological sample; b) adding a lysis solution to the biological sample to produce a mixture, wherein the lysis solution comprises a first reagent that causes the mixture to have a pH equal to or greater than 10; c) incubating the biological sample with the lysis solution for up to 5 minutes to produce a lysate; and d) adding a second reagent to the lysate to lower the pH of the lysate to a level at which the RNA is stable. The lysis solution may comprise the first reagent and the reducing agent, such that the first reagent and the reducing agent are added simultaneously to the biological sample. Alternatively, the reducing agent and the first reagent can be added separately to the biological sample.

The biological sample containing RNA can be any sample of cells, tissue, or fluid isolated from a prokaryotic or eukaryotic organism, including but not limited to, for example, blood, plasma, serum, fecal matter, urine, bone marrow, bile, spinal fluid, lymph fluid, sputum, ascites, bronchial lavage fluid, synovial fluid, samples of the skin, external secretions of the skin, respiratory, intestinal, and genitourinary tracts, tears, saliva, milk, organs, biopsies, and also samples of cells, including cells from bacteria, fungi, protists, plants, and animals as well as in vitro cell culture constituents, including but not limited to, conditioned media resulting from the growth of cells and tissues in culture medium, e.g., recombinant cells, and cell components, and also samples containing nucleic acids from viruses. In particular, this method can be used to prepare RNA from RNase-rich sources, such as RNase-rich tissues (e.g., pancreas, liver, spleen, and thymus), cells (e.g., leukocytes, monocytes and macrophages), and bodily fluids (e.g., blood).

The first reagent used in the lysis solution may be a strong base, a weak base, or an amphoteric compound, such as an ampholyte. Exemplary strong bases include potassium hydroxide (KOH), sodium hydroxide (NaOH), barium hydroxide (Ba(OH)$_2$), cesium hydroxide (CsOH), strontium hydroxide (Sr(OH)$_2$), calcium hydroxide (Ca(OH)$_2$), lithium hydroxide (LiOH), and rubidium hydroxide (RbOH). Exemplary weak bases include Tris (tris(hydroxymethyl)aminomethane), N-ethylmorpholine, bis-tris-propane, creatine, imidazole, ammediol, arginine, lysine, ammonia, methylamine, dimethylamine, trimethylamine, diethylamine, diethylmethylamine, ethanolamine, and isoamylamine. In certain embodiments, the first reagent is an electrochemically generated base.

The reducing agent may be a thiol, such as, but not limited to, dithiothreitol (DTT), 2-mercaptoethanol (BME), and Tris (2-carboxyethyl)phosphine (TCEP). The amount of the reducing agent added to the biological sample will depend on the particular reducing agent used, but should be sufficient to inactivate RNases in the biological sample.

The second reagent, which is added to the lysate, can be a strong acid, a weak acid, or an amphoteric compound, such as an ampholyte. Exemplary strong acids include hydrochloric acid, perchloric acid, sulfuric acid, nitric acid, and hydrobromic acid. Exemplary weak acids include MOPS (3-(N-morpholino)propanesulfonic acid), MES (2-(N-morpholino) ethanesulfonic acid), PIPES (piperazine-N,N'-bis(2-ethanesulfonic acid)), HEPES ((4-(2-hydroxyethyl)-1-piperazineethanesulfonic acid)), TAPS (3-[[1,3-dihydroxy-2-(hydroxymethyl)propan-2-yl]amino]propane-1-sulfonic acid), tricine (N-(2-hydroxy-1,1-bis(hydroxymethyl)ethyl) glycine), cysteine, cacodylic acid, phosphoric acid, acetic acid, citric acid, formic acid, nitrous acid, carbonic acid, capric acid, caproic acid, and caprylic acid. In certain embodiments, the second reagent is an electrochemically generated acid.

In certain embodiments, the second reagent is added to the lysate after at least 5 seconds and up to 5 minutes after addition of the lysing solution, including any amount of time within this range, including at 1 minute, 2 minutes, 3 minutes, 4 minutes, or 5 minutes after addition of the lysing solution. The amount of the second reagent added to the lysate should be sufficient to lower the pH to a level at which the RNA is stable. The final pH of the lysate after adding the second reagent is preferably between pH 6 and pH 8.

In certain embodiments, the acid or base added to the biological sample is generated electrochemically. In aqueous solution, hydronium and hydroxide ions can be generated by electrolysis of water:

The hydronium and hydroxide ions so produced recombine with counter ions that are present in the aqueous solution. A selected acid or base can be produced accordingly by providing the appropriate counter ions. Alternatively, organic acids and bases can be generated by electrolysis of organic compounds in non-aqueous solution. See, e.g., U.S. Pat. No. 7,402,283, Akse et al. (1999) *On Demand Electrochemical Production Of Reagents To Minimize Resupply Of Expendables*, SAE Technical Paper 1999-01-2181; Maurer et al. (2006) PLoS One 1:e34; Volke et al. (1994) *Electrochemistry in Organic Synthesis*, Springer-Verlag; Baizer (1991) *Organic Electrochemistry An Introduction and a Guide*, M. M. Marcel Dekker Inc; herein incorporated by reference).

Additional agents may be used to facilitate extraction and improve recovery of RNA from biological samples. For example, the lysis solution may further comprise one or more additional agents, such as detergents, chelating agents, denaturants, or carrier RNA, or any combination thereof. Alternatively, any of these agents can be added to the biological sample separately from the lysis solution.

In one embodiment, a detergent is added to the biological sample. Anionic, cationic, zwitterionic, or non-ionic detergents can be used such as, but not limited to, sodium dodecyl sulfate (SDS), N-laurylsarcosine, hexadecyltrimethylammonium bromide (CTAB), sodium tri-isopropylnaphthalene sulfonate, Tween 20, Tween 40, Tween 60, Triton X-100, sodium cholate, octylglucoside, sodium deoxycholate, dodecyldimethylamine oxide, CHAPS, CHAPSO, SB3-12, SB3-14, IGEPAL CA-630, Pluroinic F-68, Nonidet P40-substitute, Brij 35, n-dodecyl-β-D-maltoside, and octyl-β-D-glucopyranoside.

In another embodiment, carrier RNA is added to the biological sample. Carrier RNA may include polyinosinic acid, poly-A RNA, bacterial ribosomal RNA, bacterial or yeast transfer RNA, or other RNA that improves the recovery of the desired RNA (see, e.g., Winslow, et al. (1991) Nucleic Acids Research 19(12):3251-3253; Wang et al. (2002) Biotechniques 33(4):788, 790, and 792; herein incorporated by reference).

In another embodiment, a chelating agent is added to the biological sample. Chelating agents that can be used include, but are not limited to, ethylene diamine tetraacetic acid (EDTA), ethylene bis(oxyethylenenitrilo)tetraacetic acid (EGTA), o-phenanthroline, and sodium 4-amino salicylate.

In another embodiment, a denaturant is added to the biological sample. Denaturants that can be used include, but are not limited to, urea, guanidine thiocyanate (GndSCN), guanidine hydrochloride (GndHCL), and lithium perchlorate.

If the biological sample comprises gram-positive bacteria, a peptidoglycan digesting enzyme (e.g., lysozyme) may be added to the biological sample before adding the reducing agent or lysing solution to aid in lysing the bacteria.

Any type of RNA can be prepared by the methods described herein, including but not limited to, messenger RNA, ribosomal RNA, transfer RNA, or regulatory RNA (e.g., small regulatory non-coding RNA, such as small interfering RNA (siRNA), microRNA (miRNA) and Piwi-associated RNAs (piRNA), and long non-coding RNA).

The methods described herein produce high quality RNA that may be used directly in numerous applications without further purification. However, if desired, RNA can be further purified for certain purposes using methods well-known in the art. For example, RNA may be further purified by immobilization on a solid support, such as silica, RNA adsorbent beads (e.g., oligo(dT) coated beads or beads composed of polystyrene-latex, glass fibers, cellulose or silica), magnetic beads, or by reverse phase, gel filtration, ion-exchange, or affinity chromatography. RNA can also be isolated from suspensions by conventional methods, such as phenol-chloroform extraction or precipitation with alcohol. Alternatively, an electric field-based method can be used to separate the desired RNA molecule from other molecules. Exemplary electric field-based methods include polyacrylamide gel electrophoresis, agarose gel electrophoresis, capillary electrophoresis, pulsed field electrophoresis, and isotachophoresis. See, e.g., *RNA: Methods and Protocols* (Methods in Molecular Biology, edited by H. Nielsen, Humana Press, 1st edition, 2010); Rio et al. *RNA: A Laboratory Manual* (Cold Spring Harbor Laboratory Press; 1st edition, 2010); Farrell *RNA Methodologies: Laboratory Guide for Isolation and Characterization* (Academic Press; 4$^{th}$ edition, 2009); Zähringer (2012) Lab Times (2-2012):52-63; Garcia-Schwarz et al. (2012) Journal of Visualized Experiments 61:e3890; Rogacs et al. (2012) Anal. Chem. 84(14):5858-5863; Hagan et al. (2009) Anal Chem. 81(13):5249-5256; Righetti (2005) J. Chromatogr. A10 79(1-2):24-40; Gebauer et al. (2011) Electrophoresis 32(1):83-89; herein incorporated by reference in their entireties.

RNA samples prepared by the methods described herein can be used for various purposes, including but not limited to PCR, ligation, transcriptome analysis, microarray analysis, northern analysis, and cDNA library construction.

B. Kits

In another aspect, the invention provides kits that can be used to prepare RNA from biological samples. For example, the kits can be used to prepare RNA from prokaryotic or eukaryotic organisms or viruses. The kit may include a lysis solution, as described herein, or reagents for preparing a lysis solution, a container for holding a biological sample; and printed instructions for using the lysis solution with the biological sample or a portion of the biological sample to extract RNA from the biological sample. The kit may further comprise one or more additional agents for RNA extraction (e.g., detergents, chelating agents, denaturants, or carrier RNA) or agents for purification of RNA (e.g., RNA-adsorbent beads, magnetic beads, silica, or gel filtration, ion exchange, or affinity chromatography media). In addition, kits may include agents for analyzing or quantifying the RNA. Such kits may also include components that preserve or maintain RNA or that protect against its degradation. Such components may be RNase-free or protect against RNases.

The kit can comprise one or more containers for compositions contained in the kit. The components of the kit may be packaged in separate containers. Compositions can be in liquid form or can be lyophilized. Suitable containers for the compositions include, for example, bottles, vials, syringes, and test tubes. Containers can be formed from a variety of materials, including glass or plastic. The kit can also comprise a package insert containing written instructions for methods of preparing RNA. The instructions may include variations of the lysing protocol and describe the use of components not included in the kit.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Method of Preparing RNA from Ribonuclease (RNase)-Rich Sources

A new protocol for preparing RNA from RNase-rich sources is described that avoids degradation of RNA during and after cell lysis. The lysis protocol for RNase containing samples uses an initially high pH above 10, which accelerates cell lysis, and a reducing agent, which inactivates RNase by reducing disulfide bonds. A brief incubation for up to five minutes at high pH is followed by quenching of the sample by lowering the pH. Each of these steps can be performed by simply adding reagents with no buffer exchanges required.

Figure 1:
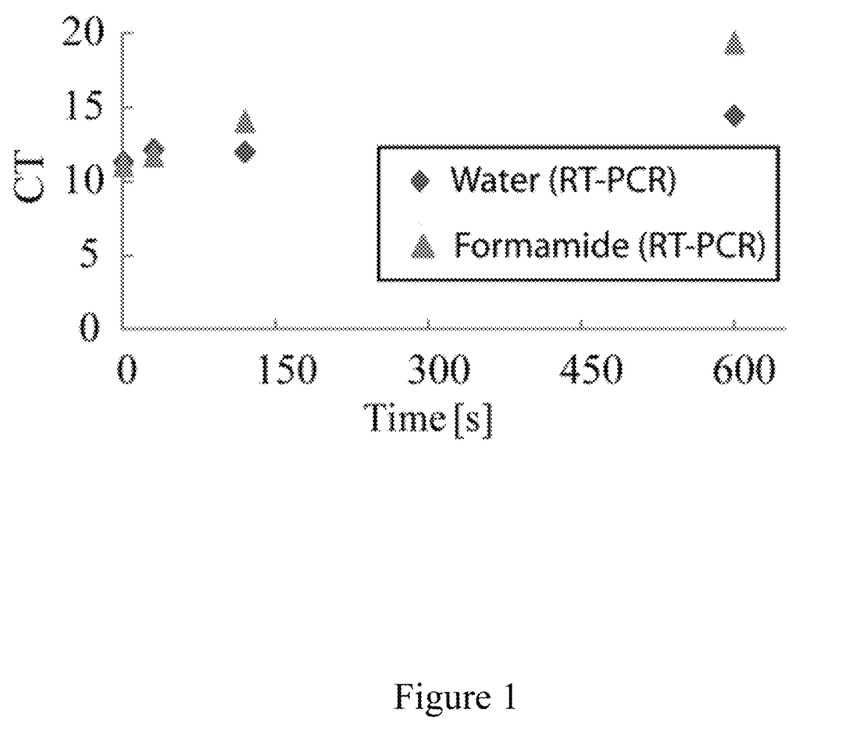
FIG. 1 shows quantitative real time polymerase chain reaction (RT-qPCR) threshold cycles for samples of pre-purified total RNA from E. coli subjected to incubation at high pH (>12) for various lengths of time. CT is the RT-PCR threshold cycle at which amplification of 16S rRNA was achieved. Longer incubation times resulted in a higher CT, which indicates a higher degree of RNA degradation.
Figure 2:
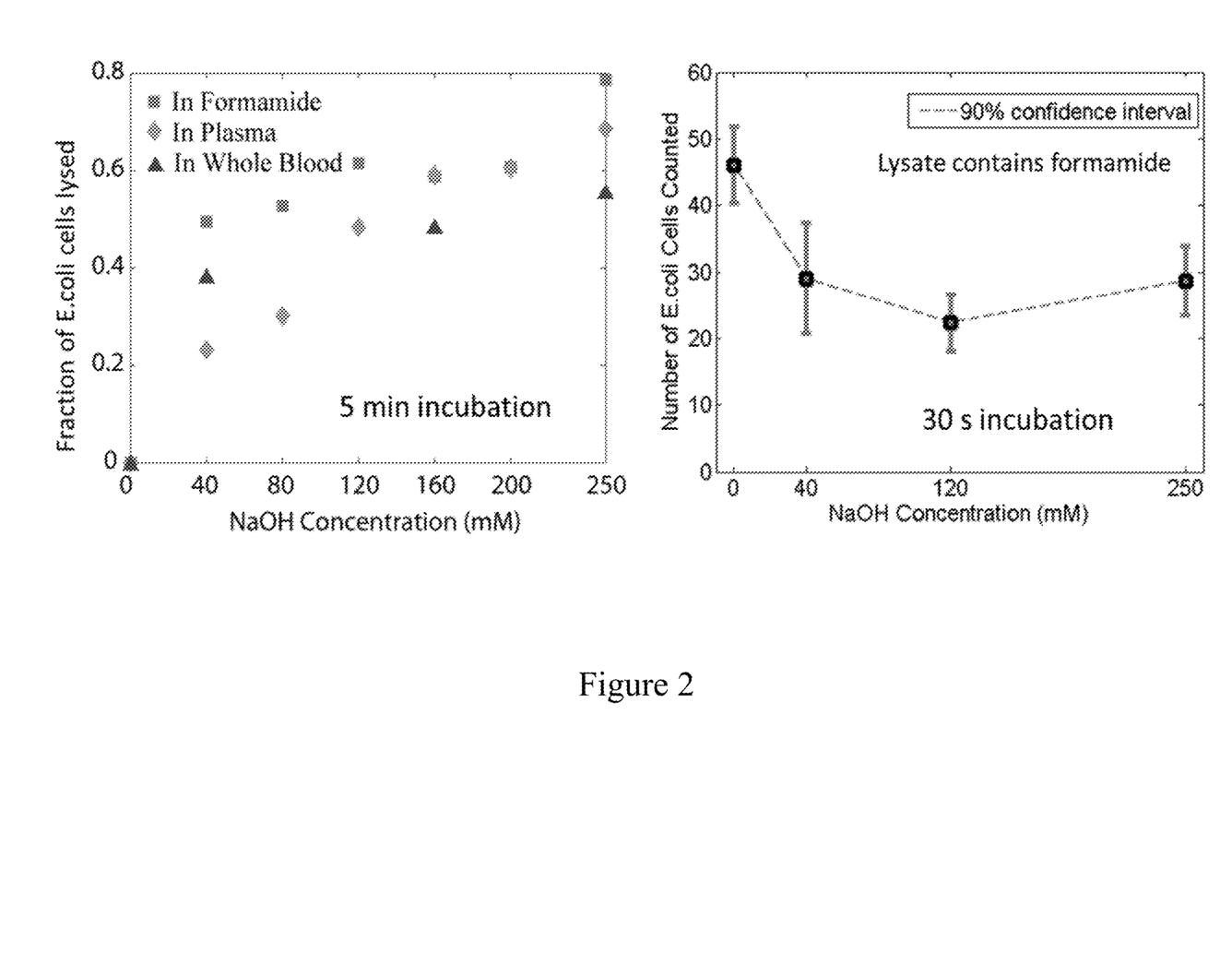

We were concerned that the brief incubation with NaOH might contribute to some RNA degradation, but found that it had a negligible effect on RT-qPCR amplification of our target RNA sequences. For example, we found negligible differences in RT-qPCR threshold cycles for samples of 16S rRNA that had been purified with a standard SPE column (PureLink RNA Mini kit from Life Technologies Corp., Carlsbad, Calif.) with and without treatment with 125 mM NaOH for 1 minute (see FIG. 1). With respect to lysing, we found through repeated trials and lysing quantitation studies that a 30 second incubation of gram-negative cells showed similar lysing performance to longer incubations of up to 5 minutes with 130 mM NaOH (see FIG. 2).

We used a reducing agent to eliminate RNase activity, which depends on the disulfide bonds of the enzyme remaining intact. Although NaOH by itself reduces the disulfide bonds of RNase with a half-life of about 30 minutes in 0.2 M NaOH (Florence (1980) Biochem. J. 189(3):507-520), prolonged incubation of samples under alkaline conditions degrades RNA. The removal of RNase disulfide bonds can be greatly accelerated by combining alkali lysis with reducing agents (e.g., DTT). The addition of a reducing agent reduces the time needed to eliminate disulfide bonds to under 5 minutes. At moderate pH (e.g., about pH 9), loss of RNase activity with reducing agents is slow, but when the pH is increased to about 13.5, hydroxide ions, acting in concert with the reducing agent, accelerate the cleavage of disulfide bonds by about 300-fold (Lu et al. (2010) Analytical Biochemistry 405(1): 67-72). The combination of a reducing agent and high pH triggers the covalent destruction of sulfhydryl groups and disulfide bonds by a base-catalyzed β-elimination mechanism, leading to the permanent and irreversible inactivation of RNase and other disulfide containing proteins (Lu et al., supra).

Accordingly, we chose to use a reducing agent at high pH to ensure rapid destruction of disulfide bonds in the lysing protocol. Cell lysis is performed prior to RNA extraction followed by rapid quenching of the sample by lowering the pH before the RNA has time to degrade. This method of RNA extraction has many advantages over existing methods of RNA preparation, including that cell lysis is efficient, RNases are rapidly inactivated, and sample incubation times are short (less than 5 minutes), which protects RNA from degradation. The lysing procedure is performed entirely in aqueous solution with no heating, precipitations, or buffer exchanges required. Thus, we provide a quick, simple procedure for extracting RNA, which can easily be automated. The resulting RNA suspension may be directly compatible with downstream assays, or if desired, RNA can be further purified using standard purification protocols.

Variations of the Lysis Protocol

Figure 3:
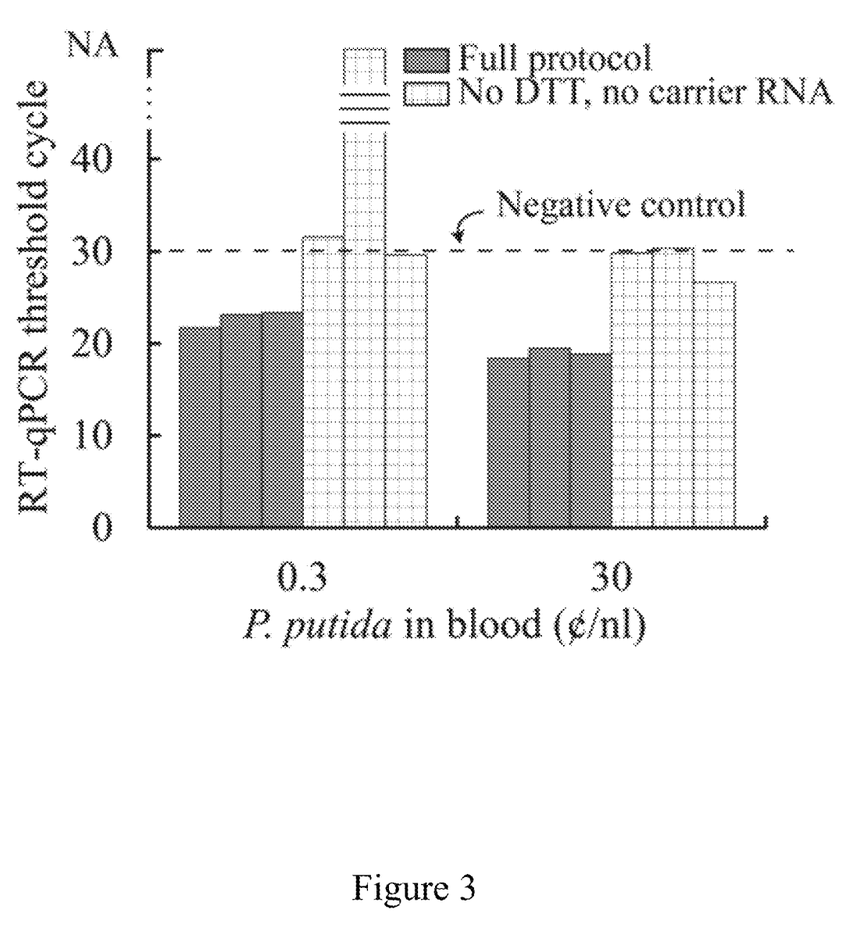

In variations of the lysis protocol, additional agents may be used, such as surfactants, carrier RNA, or denaturants. Surfactants may be added to facilitate lysis of cells and inactivation of RNase. Carrier RNA may be added after quenching of the lysate to inhibit the activity of any remaining ribonucleases. By "carrier RNA" is meant exogenous RNA that is added to a sample to provide a competitive RNase substrate to reduce degradation of target RNA (see, e.g., Winslow et al. (1991) 19(12):3251-3253). Addition of carrier RNA to lysates has been shown to enhance the recovery of trace amounts of DNA and RNA by ethanol precipitation and SPE-based extraction (Gallagher et al. (1987) Biochemical and Biophysical Research Communications 144(1):271-276; Rio et al. (2010) Cold Spring Harbor Protocols (6); Shaw et al. (2009) Analytica Chimica Acta 652(1-2):231-233; Bhattacharyya et al. (2008) Sensors and Actuators B: Chemical 129(2):693-698). The results of experiments showing the combined effect of both DTT and carrier RNA on target RNA stability and recovery are shown in FIG. 3.

For matrices highly abundant in RNases (e.g., blood), a denaturant may be added to facilitate inactivation of RNases. The combination of a denaturant, high pH, and a reducing agent can irreversibly inactivate RNase in less than 20 seconds (Lu et al. (2010) Analytical Biochemistry 405(1):67-72).

For complex matrices containing large concentration of proteins, and phospholipids, addition of detergents may help to maintain solubility. Addition of detergents has also been shown to aid lysis of gram-positive bacteria (Liao et al. (2007) J. Mol. Diagn. 9(2):158-168).

For samples containing gram-positive bacteria, a peptidoglycan digesting enzyme may be used. Gram-positive bacteria contain many layers of a peptidoglycan (polymer consisting of sugars and amino acids), and do not possess a lipid outer membrane. To lyse gram-positive bacteria, a peptidoglycan digesting enzyme, such as lysozyme, should be added prior to alkali-lysis. Incubation of lysozyme with a cell suspension for about 5 minutes has been shown to increase RNA extraction efficiency (Liao et al., supra). Lysozyme is added before the alkali-reducing incubation step because lysozyme contains disulfide bonds, which will irreversibly be inactivated during alkali-lysis.

Exemplary Lys is Protocols

In one example, the lysis buffer components are added to the biological sample as follows: A solution containing a reducing agent (e.g., DTT) and a strong base at a pH>10 (e.g., NaOH) is added to the biological sample. This solution may also contain carrier RNA (i.e., "decoy RNA") and surfactants (e.g., Triton X-100, SDS, etc.). After exposure of the biological sample to high pH, the sample is quenched with a weak acid, which also acts as a buffer (so that the strong base cation becomes a titrant to the added acid and the addition achieves a lower pH).

Alternatively, components are added in discrete steps in different orders. For example, carrier RNA may be added first, then reducing agent, followed by the strong base. In another example, a mixture of carrier RNA and reducing agent is added followed by the addition of a strong base. In yet another example, lysis buffer containing a reducing agent and a weak base at sufficient concentration to yield a pH greater than 10 may be used. After incubation for up to 5 minutes, a strong acid is added to quench the sample, raising the pH to protect against RNA degradation.

RNA Purification

The lysis protocol can be designed such that the resulting RNA suspension contains reagents that are compatible with most standard downstream molecular assays. For example, the reducing agent, DTT, at concentrations below 10 mM has a stabilizing effect on enzyme activity. Therefore if the lysate contains DTT, the final concentration of DTT is preferably kept below 10 mM.

For RT-PCR, additional purification of the RNA suspension may be required, especially if the RNA is derived from sources abundant in PCR inhibitors. For example, AmpliTaq Gold, Taq DNA polymerases are inhibited by $Fe^{3+}$, $Mg^{2+}$, $Ca^{2+}$, $Na^+$, $K^+$, lactoferrin, hemoglobin and immunoglobin (Al-Soud et al. (2001) Journal of Clinical Microbiology 39(2):485-493).

Extracted RNA can be purified in a variety of ways, including, for example, by immobilization of RNA on a solid support (e.g., silica in the presence of a chaotropic agent), extraction with an organic solvent such as phenol or chloroform, alcohol precipitation, magnetic beads, or electric field based purification of nucleic acids, such as by isotachophoresis (ITP) (Rogacs et al. (2012) Analytical Chemistry 84(14): 5858-5863).

Isotachophoresis (ITP) offers an alternative approach for nucleic acid purification. The input and output reagents used in ITP can be compatible, respectively, with lysis and RNase control as described herein, and amplification. ITP does not require specific surfaces, specialized geometries, or pumping of reagents. It uses an electric field to extract and preconcentrate only target analytes whose electrophoretic mobility is bracketed between the anions of its trailing (TE) and leading electrolytes (LE). Anionic inhibitors with mobilities lower than of the TE do not focus, but do electrophorese into the microchannel. The separation distance between these potentially PCR-inhibiting contaminants and the focused nucleic acid in the ITP zone increases over time. For a channel length, L, the separation distance between the ITP and the inhibitor zone front, $\Delta L$ can be expressed as $\Delta L=(1-\mu_i/\mu_{TE})L$, where $\mu_i$ and $\mu_{TE}$ are the inhibitor and TE anion mobilities, respectively. For example, the zone front of an inhibitor with mobility $\mu_i=0.9\mu_{TE}$ will lag 0.6 cm behind the ITP zone at the end of our 6 cm microchannel. ITP is a highly sensitive, robust sample preparation method, which under ideal conditions can provide up to one million-fold concentration (Jung et al. (2006) Analytical Chemistry 79(1):345-349; Bahga et al. (2011) Electrophoresis 32(5):563-572; Garcia-Schwarz et al. (2012) J. Vis. Exp. (61):e3890; Boček, P., Analytical isotachophoresis. Springer Berlin/Heidelberg: 1981; Vol. 95, pp 131-177; Jung et al. (2006) Analytical Chemistry 78(7):2319-2327).

While the preferred embodiments of the invention have been illustrated and described, it will be appreciated that various changes can be made therein without departing from the spirit and scope of the invention.

What is claimed is:

1. A method of preparing RNA from a biological sample, the method comprising performing the following steps:
    a) adding a reducing agent to the biological sample;
    b) adding a lysis solution to the biological sample to produce a mixture, wherein the lysis solution comprises a first reagent that causes the mixture to have a pH equal to or greater than 10;
    c) incubating the biological sample with the lysis solution for up to 5 minutes to produce a lysate; and
    d) adding a second reagent to the lysate to lower the pH of the lysate to a level at which the RNA is stable;
    wherein steps (a)-(d) are performed without heating the biological sample and in the absence of other additional agents that inhibit polymerases or reverse transcriptases.

2. The method of claim 1, wherein the lysis solution comprises the first reagent and the reducing agent, wherein the first reagent and the reducing agent are added simultaneously to the biological sample.

3. The method of claim 1, wherein the reducing agent is added separately from the first reagent to the biological sample.

4. The method of claim 1, wherein the first reagent is added to the biological sample by an electrochemical reaction at an electrode in order to raise the pH of the biological sample.

5. The method of claim 1, wherein the second reagent is added to the biological sample by an electrochemical reaction at an electrode in order to lower the pH of the biological sample.

6. The method of claim 1, wherein the second reagent is added to the lysate within 2 minutes after adding the lysis solution.

7. The method of claim 1, wherein the second reagent is added to the lysate within 3 minutes after adding the lysis solution.

8. The method of claim 1, further comprising adding lysozyme to the biological sample before adding the reducing agent.

9. The method of claim 1, wherein the first reagent is a strong base, a weak base, or an ampholyte.

10. The method of claim 9, wherein the strong base is selected from the group consisting of potassium hydroxide (KOH), sodium hydroxide (NaOH), barium hydroxide (Ba(OH)$_2$), cesium hydroxide (CsOH), strontium hydroxide (Sr(OH)$_2$), calcium hydroxide (Ca(OH)$_2$), lithium hydroxide (LiOH), and rubidium hydroxide (RbOH).

11. The method of claim 9, wherein the weak base is selected from the group consisting of Tris (tris(hydroxymethyl)aminomethane), N-ethylmorpholine, bis-tris-propane, creatine, imidazole, ammediol, arginine, lysine, ammonia, methylamine, dimethylamine, trimethylamine, diethylamine, diethylmethylamine, ethanolamine, and isoamylamine.

12. The method of claim 1, wherein the pH of the lysate after adding the second reagent is between pH 6 and pH 8.

13. The method of claim 1, wherein the second reagent is a strong acid, a weak acid, or an ampholyte.

14. The method of claim 13, wherein the strong acid is selected from the group consisting of hydrochloric acid, perchloric acid, sulfuric acid, nitric acid, and hydrobromic acid.

15. The method of claim 13, wherein the weak acid is selected from the group consisting of MOPS (3-(N-morpholino)propanesulfonic acid), MES (2-(N-morpholino)ethanesulfonic acid), PIPES (piperazine-N,N'-bis(2-ethanesulfonic acid)), HEPES ((4-(2-hydroxyethyl)-1-piperazineethanesulfonic acid)), TAPS (3-[[1,3-dihydroxy-2-(hydroxymethyl)propan-2-yl]amino]propane-1-sulfonic acid), tricine (N-(2-hydroxy-1,1-bis(hydroxymethyl)ethyl)glycine), cysteine, cacodylic acid, phosphoric acid, acetic acid, citric acid, formic acid, nitrous acid, carbonic acid, capric acid, caproic acid, and caprylic acid.

16. The method of claim 1, wherein the reducing agent is a thiol.

17. The method of claim 16, wherein the thiol is selected from the group consisting of dithiothreitol (DTT), 2-mercaptoethanol (BME), and Tris(2-carboxyethyl)phosphine (TCEP).

18. The method of claim 1, further comprising adding a detergent to the biological sample.

19. The method of claim 18, wherein the detergent is anionic, cationic, zwitterionic, or non-ionic.

20. The method of claim 19, wherein the detergent is selected from the group consisting of sodium dodecyl sulfate (SDS), N-laurylsarcosine, hexadecyltrimethylammonium bromide (CTAB), sodium tri-isopropylnaphthalene sulfonate, Tween 20, Tween 40, Tween 60, Triton X-100, sodium cholate, octylglucoside, sodium deoxycholate, dodecyldimethylamine oxide, CHAPS, CHAPSO, SB3-12, SB3-14, IGEPAL CA-630, Pluroinic F-68, Nonidet P40-substitute, Brij 35, n-dodecyl-β-D-maltoside, and octyl-β-D-glucopyranoside.

21. The method of claim 1, further comprising adding carrier RNA to the biological sample.

22. The method of claim 21, wherein the carrier RNA is selected from the group consisting of polyinosinic acid, poly-A RNA, bacterial ribosomal RNA, bacterial transfer RNA, and yeast transfer RNA.

23. The method of claim 1, further comprising adding a chelating agent to the biological sample.

24. The method of claim 23, wherein the chelating agent is selected from the group consisting of ethylene diamine tetraacetic acid (EDTA), ethylene bis(oxyethylenenitrilo)tetraacetic acid (EGTA), o-phenanthroline, and sodium 4-aminosalicylate.

25. The method of claim 1, further comprising adding formamide to the biological sample.

26. The method of claim 1, further comprising adding a denaturant to the biological sample.

27. The method of claim 26, wherein the denaturant is selected from the group consisting of urea, guanidine thiocyanate (GndSCN), guanidine hydrochloride (GndHCL), and lithium perchlorate.

28. The method of claim 1, wherein the biological sample comprises cells, tissue, or a bodily fluid.

29. The method of claim 28, wherein the bodily fluid is selected from the group consisting of blood, serum, plasma, urine, saliva, sputum, ascites, semen, bronchial lavage fluid, synovial fluid, and cerebrospinal fluid.

30. The method of claim 1, wherein the biological sample comprises conditioned cell culture media.

31. The method of claim 1, wherein the RNA comprises messenger RNA, ribosomal RNA, transfer RNA, or regulatory RNA.

32. The method of claim 1, wherein the RNA is eukaryotic RNA or prokaryotic RNA.

33. The method of claim 32, wherein the RNA comprises animal RNA, bacterial RNA, fungal RNA, protist RNA, or plant RNA.

34. The method of claim 33, wherein the RNA comprises human RNA.

35. The method of claim 1, wherein the RNA comprises viral RNA.

36. The method of claim 1, further comprising amplifying at least one RNA in the biological sample.

37. The method of claim 1, further comprising isolating the RNA.

38. The method of claim 37, wherein the RNA is isolated by immobilization on a solid support.

39. The method of claim 38, wherein the solid support is RNA adsorbent beads or magnetic beads.

40. The method of claim 38, wherein the solid support is silica.

41. The method of claim 37, wherein the RNA is isolated by phenol-chloroform extraction.

42. The method of claim 37, wherein the RNA is isolated by precipitation with alcohol.

43. The method of claim 37, wherein the RNA is isolated by an electric field-based method of separation.

44. The method of claim 43, wherein the electric field-based method is selected from the group consisting of polyacrylamide gel electrophoresis, agarose gel electrophoresis, capillary electrophoresis, pulsed field electrophoresis, and isotachophoresis.

45. The method of claim 1, further comprising concentrating the RNA.

46. A method of preparing RNA from a biological sample, the method consisting of performing the following steps:
   a) adding a reducing agent to the biological sample;
   b) adding a lysis solution to the biological sample to produce a mixture, wherein the lysis solution comprises a first reagent that causes the mixture to have a pH equal to or greater than 10;
   c) incubating the biological sample with the lysis solution for up to 5 minutes to produce a lysate; and d) adding a second reagent to the lysate to lower the pH of the lysate to a level at which the RNA is stable;
wherein steps (a)-(d) are performed without heating the biological sample and in the absence of other additional agents that inhibit polymerases or reverse transcriptases.

* * * * *